United States Patent [19]
Kuhlman

[11] Patent Number: 5,693,068
[45] Date of Patent: Dec. 2, 1997

[54] SCAR-REDUCING FRAME

[76] Inventor: Marika A. Kuhlman, 12024—93rd Ave. NE., Kirkland, Wash. 98034

[21] Appl. No.: 731,773
[22] Filed: Oct. 17, 1996
[51] Int. Cl.$^6$ ............................................. A61F 13/00
[52] U.S. Cl. ............................................. 606/201; 604/304
[58] Field of Search ......................... 128/155–156, 128/149, 888, 132; 604/304, 307

[56] References Cited

U.S. PATENT DOCUMENTS

| | | | |
|---|---|---|---|
| 1,920,808 | 8/1933 | Sander | 128/156 |
| 2,443,140 | 6/1948 | Larsen | 128/888 |
| 4,038,989 | 8/1977 | Romero-Sierra et al. | 128/335 |
| 4,053,053 | 10/1977 | Tumangday | 128/155 |
| 4,341,207 | 7/1982 | Steer et al. | 128/156 |
| 4,399,816 | 8/1983 | Spangler | 128/888 |
| 4,561,435 | 12/1985 | McKnight et al. | 128/156 |
| 4,614,183 | 9/1986 | McCracken | 128/155 |
| 4,706,661 | 11/1987 | Barrett | 128/155 |
| 4,732,146 | 3/1988 | Fasline et al. | 128/155 |
| 4,865,026 | 9/1989 | Barrett | 128/155 |
| 5,056,510 | 10/1991 | Gilman | 128/155 |
| 5,176,703 | 1/1993 | Peterson | 606/216 |
| 5,234,462 | 8/1993 | Pavletic | 606/215 |
| 5,244,457 | 9/1993 | Karami et al. | 602/55 |
| 5,437,623 | 8/1995 | McClees et al. | 602/59 |

Primary Examiner—Michael Buiz
Assistant Examiner—Nancy Connolly Mulcare
Attorney, Agent, or Firm—Seed and Berry LLP

[57] ABSTRACT

A scar-reducing frame structure of the type for preventing motion relative to a healing cut in a person's skin of skin the region of the cut. The frame is conformable and attachable to the person's skin, and has an open area which encompasses the cut. The frame is substantially rigid in the plane of the frame so as to substantially prevent motion of the skin within the open area relative to the cut to allow the cut to heal without scarring. The frame includes an adhesive layer for fixedly attaching the frame to the skin. The adhesive layer is waterproof and provides for secure attachment of the frame to the skin, and allows the frame structure to be removed for purposes of replacement or when healing of the cut is complete.

20 Claims, 2 Drawing Sheets

SCAR-REDUCING FRAME

TECHNICAL FIELD

The present invention is directed toward an apparatus for facilitating in the healing of a wound or cut and, more particularly, toward an apparatus for reducing scarring as the wound or cut heals.

BACKGROUND OF THE INVENTION

Cuts made in a person's skin, whether as a result of a surgical procedure or an inadvertent act, often heal in such a manner as to leave unsightly scars. Such scars are particularly undesirable where incisions are made during the course of cosmetic surgery, or where incisions are made on readily visible portions of a person's body. One cause of scarring during the healing of a cut is movement of the patient's skin at and around the cut, causing the cut to be partially or fully reopened, which often damages the portions of the skin that had begun healing. Accordingly, such movement of the patient's skin at and around the cut lengthens the healing process and greatly increases the risk of formation of a visible scar.

Various devices have been employed to draw the skin on opposing sides of cuts, such as an incision, together. For example, stitches are commonly used to close cuts in the skin. Other examples of such devices include adhesive clamps, as described in U.S. Pat. No. 4,706,661, adhesive straps, as described in U.S. Pat. No. 5,234,462, wire networks, as described in U.S. Pat. No. 5,176,703, radially tensioned rings, as described in U.S. Pat. No. 4,865,026, and strapped frames, as described in U.S. Pat. No. 4,732,146. Other devices are directed toward maintaining bandages in contact with the wounded area, such as the mesh and ring described in U.S. Pat. No. 5,437,623. However, none of the foregoing devices are directed toward immobilizing skin in the region of a cut in order to prevent or reduce scarring as the cut heals.

SUMMARY OF THE INVENTION

The present invention provides a frame structure that substantially prevents movement of skin in an area surrounding a cut in the skin relative to the cut. In this manner, the skin at the cut is allowed to heal in such a way as to minimize scarring during the healing process.

In a preferred embodiment of the present invention, the frame structure includes a substantially rigid frame which has an open interior area. The frame is shaped and sized to completely surround a cut in a person's skin, with the entire cut being in the open interior area. An adhesive layer is attached to the lower surface of the frame for securely adhering the substantially rigid frame to the person's skin. The substantially rigid frame defines a frame plane, and the frame is sufficiently rigid in the frame plane to prevent movement of the skin relative to the cut under the frame and in the interior area. The frame is sufficiently flexible in a plane normal to the frame plane so that it may easily conform to the contour of the person's skin when the frame structure is affixed.

In the preferred embodiment of the invention, the adhesive on the lower layer of the substantially rigid frame has a shape corresponding to the shape of the frame so the adhesive does not extend into the open interior area. A removable release layer is provided to cover the lower surface of the adhesive before the frame structure is applied to the person's skin in order to prevent the adhesive from becoming contaminated prior to such application.

The invention also provides a method for substantially preventing the movement of a person's skin in an area surrounding a cut in the skin relative to the cut so as to minimize scarring during healing of the cut. The method comprises positioning a substantially rigid frame structure on the person's skin adjacent to the cut, securing the frame structure to the skin such that the cut is located within an open portion of the frame, and preventing movement of the skin surrounding the cut relative to the cut to permit the cut to heal.

These and other aspects of this invention will become evident upon reference to the following detailed description and attached drawings.

DETAILED DESCRIPTION OF THE INVENTION

Figure 2:
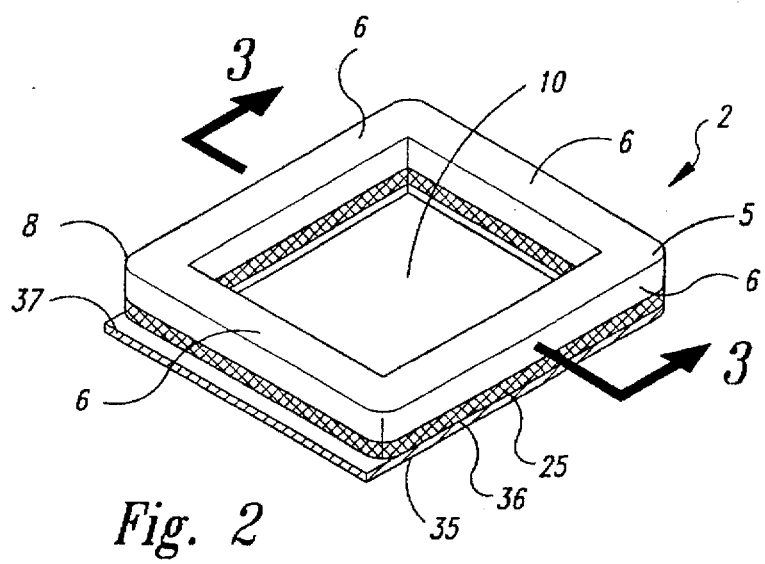
FIG. 2 is a top isometric view of the scar-reducing frame of FIG. 1 shown removed from the person's skin and shown with a release layer thereon.
Figure 3:
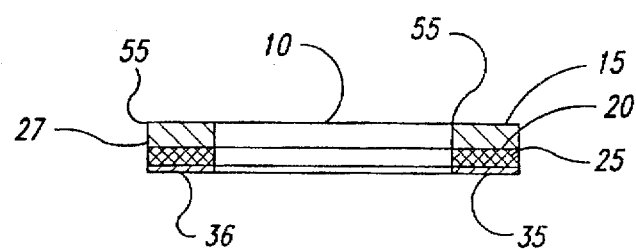
FIG. 3 is a cross-sectional view taken substantially along line 3—3 of FIG. 2.
Figure 1:
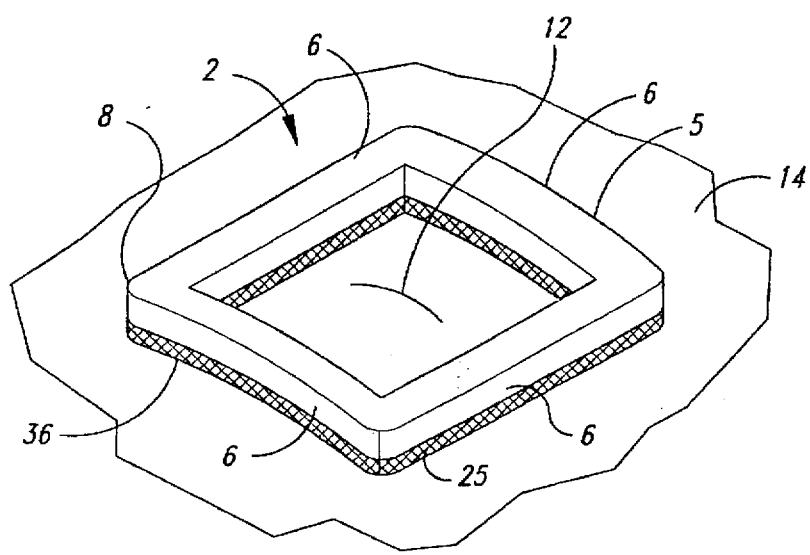
FIG. 1 is a top isometric view of a scar-reducing frame structure in accordance with a preferred embodiment of the invention, shown positioned on a patient's skin around a cut.

A scar-reducing frame structure 2 in accordance with a preferred embodiment of the present invention is shown in FIGS. 1–3 for purposes of illustration. As is seen in FIG. 1, the scar-reducing frame structure 2 includes a substantially rigid frame portion 5 having a plurality of side portions 6 interconnected to define an open center area 10. The side portions 6 are interconnected to form rounded corners 8 which minimize the potential for the frame structure 2 to catch on clothing or scratch body parts which might come into contact with the frame structure 2. The frame structure 2 is removably attachable to skin 14 of a patient around a cut 12 in the skin. The cut 12 referred to herein includes an incision from a surgical procedure, a slice, a tear, a scrape, or any other intentional or accidental break in the skin. When the frame structure 2 is attached to the patient's skin 14 around the cut 12, the frame structure substantially prevents movement of the skin at and around the cut, thereby allowing the cut to heal without being partially or fully reopened, which damages the portions of the skin at the cut that had begun to heal.

The frame portion 5 is shaped and sized so the side portions 6 surround the cut 12 and a portion of the patient's skin 14 around the cut, such that the cut and the surrounding portion of the skin are in the open center area 10. The frame portion 5 and the open center area 10 of the preferred embodiment illustrated in FIG. 1 are rectangular. Alternate embodiments of the frame structure 2 have other shapes, such as circular, elliptical or square, that are usable in various situations depending upon the size and shape of the cut 12, and the contour of the skin 14 around the cut to which the frame portion 5 is attached. The external shape of frame portion 5 need not correspond to the shape of the open center area 10.

As best seen in FIGS. 1 and 3, the frame portion 5 has a generally flat lower surface 20 opposite an upper surface 15. The lower surface 20 faces toward the skin 14 when the frame structure 2 is attached to the skin around the cut 12. An adhesive layer 25 is securely adhered to the lower surface 20 of the frame portion 5 and is positioned to securely affix the frame portion to the patient's skin 14 around the cut 12. Accordingly, the adhesive layer 25 is sandwiched between the frame portion 5 and the skin 14 with the portion being fixedly attached to the skin 14 and substantially non-movable relative to the cut 12.

In the preferred embodiment, the adhesive layer 25 is a waterproof, double-sided adhesive tape. However, other attaching or securing devices can be used to fixedly yet removably attach the frame portion 5 to the patient's skin 14. Examples of other attaching devices include, but are not limited to, stitching, which directly removably affixes the frame portion 5 to the patient's skin.

The preferred embodiment has the adhesive layer 25 attached to the frame portion's lower surface 20, although the adhesive layer may be attached to the frame upper surface 15 or frame side 27 to securely hold the frame portion 5 in a fixed position relative to the cut 12. The surface of frame portion 5 to which the attaching device is attached will depend upon the type of attaching device used, the size and shape of the frame portion and the contour of the skin 14.

In a preferred embodiment the frame structure 2 is affixed to the patient's skin 14 and the frame structure remains in place until the cut 12 is substantially or completely healed. The preferred adhesive layer 25 thus is waterproof so the frame portion 5 will remain securely fixed in place as the cut 12 heals in the event the adhesive layer gets wet, such as during bathing, cleaning of the cut, or even from sweat. The adhesive layer 25 is attached easily and firmly to the skin 14 and is removable when the cut 12 is healed without causing the skin to be excessively pulled which could damage the newly healed cut. The adhesive layer 25 has a shape corresponding to the frame portion 5 so the adhesive layer does not extend across the open center area 10. Accordingly, adhesive layer 25 does not contact or cover the cut 12 during the healing process.

As best seen in FIGS. 1 and 2, the frame portion 5 defines a frame plane that is substantially parallel to the patient's skin 14 around the cut 12 when the frame structure is adhered to the skin. The frame portion 5 is substantially rigid in the frame plane. The rigidity of the frame portion 5 fixedly adhered to the skin 14 around the cut 12 prevents the skin around the cut and in the open center area 10 from moving relative to the cut, thereby reducing scaring as the cut heals. The preferred frame portion 5 is stiff but has a degree of flexibility in a plane normal to the frame plane to allow the frame portion to be selectively bent or contoured, as illustrated in FIG. 1, to conform to the contour of the patient's skin 14 in the area around the cut 12. Thus, the frame structure 2 is not limited to use on only flat, non-curved, planar portions of the skin.

In the preferred embodiment, the frame portion 5 is constructed from a sheet of thin aluminum, and the side portions 6 are integrally connected together to form a unitary frame. Alternatively, the frame portion 5 can be made from other materials providing the rigidity in the frame plane to prevent the skin 14 around the cut 12 from moving relative to the cut while providing a degree of flexibility in the plane normal to the frame plane.

Once healing of the cut 12 has been completed, the frame structure 2 is removed from the skin 14. The adhesive layer 25 and the frame portion 5 are sufficiently easy to lift and peel from the skin 14 when the cut has substantially healed so as to avoid excessive stress at the newly healed cut 12.

As best seen in FIGS. 2 and 3, a release layer 35 is removably attached to a bottom surface 36 of the adhesive layer 25. The release layer protects the adhesive layer 25 from contamination by dust, dirt or liquids before the frame structure 2 is adhered to the patient's skin 14. In the preferred embodiment, the release layer 35 covers the adhesive layer 25 only without extending across the open center area 10; however, the release layer 35 may extend to cover the open center area 10 as well. At least a portion of the release layer 35 extends beyond one of the side portions 6 of the frame portion 5 so as to form tab 37 for easy gripping and removal of the release layer as frame structure 2 is prepared for use.

Prior to application of the frame structure 2 to the skin 14, the release layer 35 is removed from the adhesive layer 25 as discussed above. The scar-reducing frame structure 2 is then positioned relative to the skin 14 such that the open center area 10 completely surrounds the closed cut 12. The frame structure 2 is then placed against the user's skin 14 such that the adhesive layer's lower surface 36 contacts the user's skin 14. The frame structure 2 is then pressed against the skin 14 to ensure a tight bond between the adhesive layer 25 and the skin 14. As is seen in FIG. 1, the frame portion 5 conforms to the shape of the user's skin 14 while maintaining its rigidity in the frame plane to ensure that the skin around the cut 12 is prevented from moving relative to the cut. Although the frame portion 5 illustrated in FIGS. 2 and 3 is substantially flat prior to bonding to the user's skin 14, alternate embodiments of the frame portion are preformed to a selective contoured shape for application to contoured regions of the skin 14.

Figure 4:
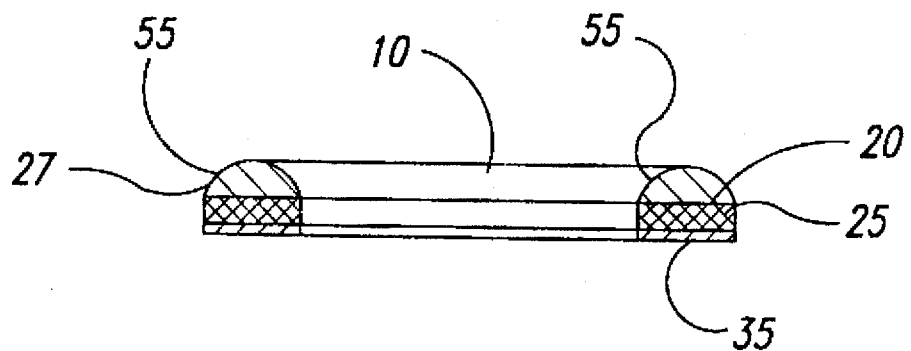
FIG. 4 is a cross-sectional view, substantially similar to FIG. 3, illustrating a scar reducing frame having rounded upper edges.
Figure 5:
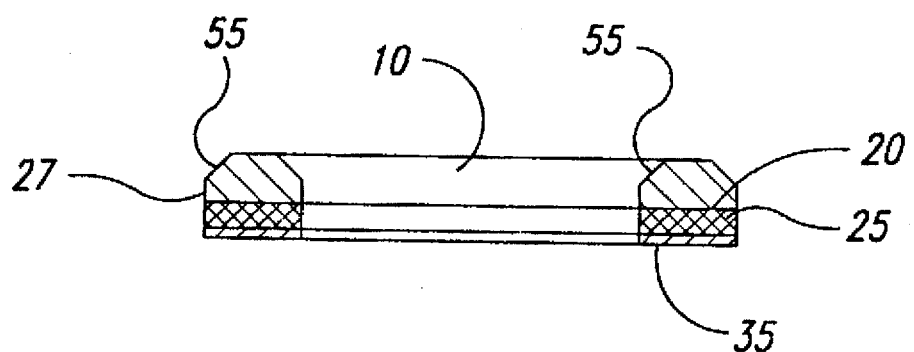
FIG. 5 is a cross-sectional view, substantially similar to FIG. 3, illustrating an alternate embodiment of a scar reducing frame having beveled upper edges.

As is best seen in FIGS. 4 and 5, alternate embodiments of the frame structure 2 include the frame portion 5 with edges 55 along the upper surface 15. The edges 55 are selectively rounded (FIG. 4) or beveled (FIG. 5) so the upper surface does not have sharp corners that, for example, may have a tendency to catch on clothing or the like.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A scar-reducing frame structure for substantially preventing movement of skin surrounding a cut in the skin, comprising:
   a non-stretchable substantially rigid frame defining an open center portion extending therethrough; and
   an attaching device attached to the frame and positioned to releasably attach the frame to the skin surrounding the cut, the attaching device and frame substantially preventing movement of the skin within a region surrounding the cut when the frame is attached to the skin, the open center portion being sized to fully surround the cut and positionable such that the cut is within the open center portion.

2. The frame structure of claim 1 wherein the frame has an upper surface and a sidewall surface connected to the upper surface at an edge, the edge being rounded.

3. The frame structure of claim 1 wherein the attaching device is an adhesive layer.

4. The frame structure of claim 1 wherein the attaching device is waterproof.

5. The frame structure of claim 1 wherein the attaching device has a shape substantially corresponding to the frame so the attaching device does not extend into the open center portion.

6. The frame structure of claim 1 wherein the frame defines a frame plane, the frame being substantially rigid in the frame plane, the frame being bendable in a direction substantially normal to the frame plane to conform to a contour of the skin around the cut.

7. The frame structure of claim 1 wherein the attaching device is a double-sided adhesive tape having opposing first and second sides and adhesive on each of the first and second sides, the first side being adhered to the substantially rigid frame.

8. A scar-reducing frame structure to minimize scarring during healing of a cut in a skin of a person, the structure being attachable to the skin for substantially preventing movement of a region of the skin surrounding the cut relative to the cut, the structure comprising:

a frame defining an open center portion and defining a frame plane, the frame being bendable in a direction substantially normal to the frame plane to conform to the person's skin, the frame being substantially rigid in the frame plane to substantially prevent movement of the skin relative to the cut; and an adhesive attached to the frame and positioned to adhere the frame to the person's skin with the cut being within the open center portion of the frame when the frame is adhered to the person's skin.

9. The frame structure of claim 8 wherein the frame comprises a plurality of frame portions interconnected to define the open center portion.

10. The frame structure of claim 9 wherein the frame portions are integrally connected forming a unitary frame.

11. The frame structure of claim 8 wherein the frame is aluminum.

12. The frame structure of claim 8 wherein the frame has an upper surface and a lower surface and the adhesive is an adhesive tape fixedly adhered to the frame lower surface.

13. The frame structure of claim 8 wherein the adhesive has a shape that substantially corresponds to the frame so the adhesive does not extend into the open center portion of the frame.

14. The frame structure of claim 8 wherein the adhesive has an exposed surface, further comprising a release layer removably attached to the exposed surface of the adhesive to protect the adhesive from contamination prior to adhering the frame to the person's skin.

15. The frame structure of claim 8 wherein the frame plane is substantially flat.

16. The frame structure of claim 8 wherein the frame plane is contoured to substantially correspond to a selected contour of the person's skin.

17. The frame structure of claim 8 wherein the substantially rigid frame has an upper surface and a sidewall surface attached to the upper surface at an edge, the edge being beveled.

18. A method for inhibiting scarring during healing of a cut in a skin of a patient, comprising the steps of:

positioning a non-stretchable substantially rigid frame on the patient's skin adjacent to the cut, the frame defining an open central portion;

securing the frame to the person's skin in a fixed position relative to the person's skin, with the cut located within the central open portion of the frame; and substantially preventing the movement of the patient's skin surrounding the cut relative to the cut after the frame is secured to the person's skin to allow the cut to heal.

19. The method of claim 18 wherein the step of securing the frame to the person's skin includes securely adhering the frame to the person's skin with an adhesive layer adhered to the frame.

20. The method of claim 18 wherein the frame has a lower surface, the lower surface having an adhesive layer attached thereto, the adhesive layer having a lower surface, the adhesive layer lower surface having a release layer, further including removing the release layer.

* * * * *